US00PP09812P

United States Patent [19]

VandenBerg

[11] Patent Number: Plant 9,812

[45] Date of Patent: Feb. 25, 1997

[54] CHRYSANTHEMUM PLANT NAMED 'YORK'

[75] Inventor: Cornelis P. VandenBerg, Salinas, Calif.

[73] Assignee: Yoder Brothers, Inc., Barberton, Ohio

[21] Appl. No.: 608,623

[22] Filed: Mar. 1, 1996

[51] Int. Cl.[6] ..... A01H 5/00

[52] U.S. Cl. ..... Plt./82.2

[58] Field of Search ..... Plt./82.2

*Primary Examiner*—Howard J. Locker

*Attorney, Agent, or Firm*—Foley & Lardner

[57] ABSTRACT

A Chrysanthemum plant named York particularly characterized by its flat capitulum form; anemone capitulum type, yellow ray floret color; diameter across face of capitulum of 57 to 64 mm when fully opened, when grown as a pinched spray pot mum; flowering response is 53 to 60 days after start of short days; medium to tall plant height, requiring 14 to 17 long days after sticking unrooted cuttings prior to start of short days and 1 to 2 applications B-9 SP to attain a flowered plant height of 25 to 33 cm when grown with 4 cuttings in a 15 cm pot; branching pattern is spreading and prolific, each plant developing 5 to 7 laterals after pinch; and recommended as a spray pot mum.

3 Drawing Sheets

The present invention comprises a new and distinct cultivar of Chrysanthemum, botanically known as *Dendranthema grandiflora,* and referred to by the cultivar name York.

York, identified as 4421 (91-386001), was originated from a cross made by Cornelis P. VandenBerg in January of 1991, in a controlled breeding program in Salinas, Calif.

The female parent of York was the cultivar identified as Forge, disclosed in U.S. Plant Pat. No. 7,470, and described as anemone spray pot mum with a yellow-orange flower color.

The male parent of York was an unnamed seedling, identified as 5581 (86-743002) and described as an anemone spray pot mum with a light pink flower color. The male parent was discarded from all programs after completion of the breeding program resulting in York.

York was discovered and selected as one flowering plant within the progeny of the stated cross by Cornelis P. VandenBerg in March of 1992, in a controlled environment in Salinas, Calif.

The first act of asexual reproduction of York was accomplished when vegetative cuttings were taken from the initial selection in May of 1992 in a controlled environment in Salinas, Calif., by technicians working under supervision of Cornelis P. VandenBerg.

Horticultural examination of controlled flowerings of successive plantings has shown that the unique combination of characteristics as herein disclosed for York are firmly fixed and are retained through successive generations of asexual reproduction.

York has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of York, which, in combination, distinguish this Chrysanthemum as a new and distinct cultivar:

1. Flat capitulum form.
2. Anemone capitulum type.
3. Yellow ray floret color.
4. Diameter across face of capitulum of 57 to 64 mm when fully opened, when grown as a pinched spray pot mum.

5. Flowering response is 53 to 60 days after start of short days.
6. Medium to tall plant height, requiring 14 to 17 long days after sticking unrooted cuttings prior to start of short days and 1 to 2 applications B-9 SP to attain a flowered plant height of 25 to 33 cm when grown with 4 cuttings in a 15 cm pot.
7. Branching pattern is spreading and prolific, each plant developing 5 to 7 laterals after pinch.
8. Recommended as a spray pot mum.

The accompanying photographic drawings show typical inflorescence and leaf characteristics of York, with the colors being as nearly true as possible with illustrations of this type.

Sheet 1 is a color photograph of York grown as a pinched spray pot mum with 4 cuttings in a 15 cm pot grown in Salinas, Calif.

Sheet 2 is a black and white photograph of three views of the inflorescence of York.

Sheet 3 is a black and white photograph showing the upper and under sides of the leaves of York at 3 stages of development (mature, intermediate and immature). In sheets 2 and 3 a measuring tape in centimeters has been added.

Of the commercial cultivars known to the inventor, the most similar in comparison to York is the female parent Forge. Reference is made to attached Chart A, which compares certain characteristics of York with the same characteristics of Forge. Similar traits are capitulum form and type, diameter across face of capitulum, and recommendation as spray pot mum. The flowering response to short days of York and Forge is comparable. The ray floret color of York is yellow (R.H.S. 13B to 13C), and slightly lighter than the yellow-orange ray floret color of Forge (R.H.S. 14A to 14B). York has a taller plant height and develops one more lateral after pinch when compared with Forge.

In the following description color references are made to The Royal Horticultural Society Colour Chart. The color values were determined on plant material grown as a pinched spray pot mum in Salinas, Calif. on May 22, 1995.

Classification:

*Botanical.*—*Dendranthema grandiflora* cv York.

*Commercial.*—Flat anemone spray pot mum.

INFLORESCENCE

A. Capitulum:

*Form.*—Flat.

*Type.*—Anemone.

*Diameter across face.*—57 to 64 mm when fully opened.

B. Corolla of ray florets:

*Color (general tonality from a distance of three meters).*—Yellow.

*Color (upper surface).*—13B to 13C.

*Color (under surface).*—13C.

*Shape.*—Straight, cross section flat, rounded petal tip.

C. Corolla of disc florets:

*Color anemone cushion (mature).*—14A.

*Color anemone cushion (immature).*—14A, tinged with 144B.

D. Reproductive organs:

*Androecium.*—Present on disc florets only; no pollen.

*Gynoecium.*—Present on both ray and disc florets.

PLANT

A. General appearance:

*Height.*—25 to 33 cm when grown with 14 to 17 long days after sticking unrooted cuttings prior to start of short days and 1 to 2 applications B-9 SP when grown with 4 cuttings in a 15 cm pot.

B. Foliage:

*Color (upper surface).*—147A.

*Color (under surface).*—147B

*Shape.*—Deeply lobed, strongly serrated.

CHART A

COMPARISON OF YORK AND FORGE

| CHARACTERISTIC | YORK | FORGE |
|---|---|---|
| Ray floret color | Yellow | Yellow-orange |
| Capitulum form and type | Flat Anemone | Flat Anemone |
| Diameter across face of capitulum | 57 to 64 mm | 57 to 64 mm |
| Branching pattern | Spreading 5 to 7 breaks | Spreading 4 to 6 breaks |
| Plant height | 25 to 33 cm | 23 to 28 cm |
| Flowering response to short days | 53 to 60 days | 54 to 60 days |

COMPARISONS MADE OF PLANTS GROWN AS PINCHED SPRAY POT MUMS IN SALINAS, CALIFORNIA

What is claimed is:

1. A new and distinct Chrysanthemum plant named York, as described and illustrated.

* * * * *

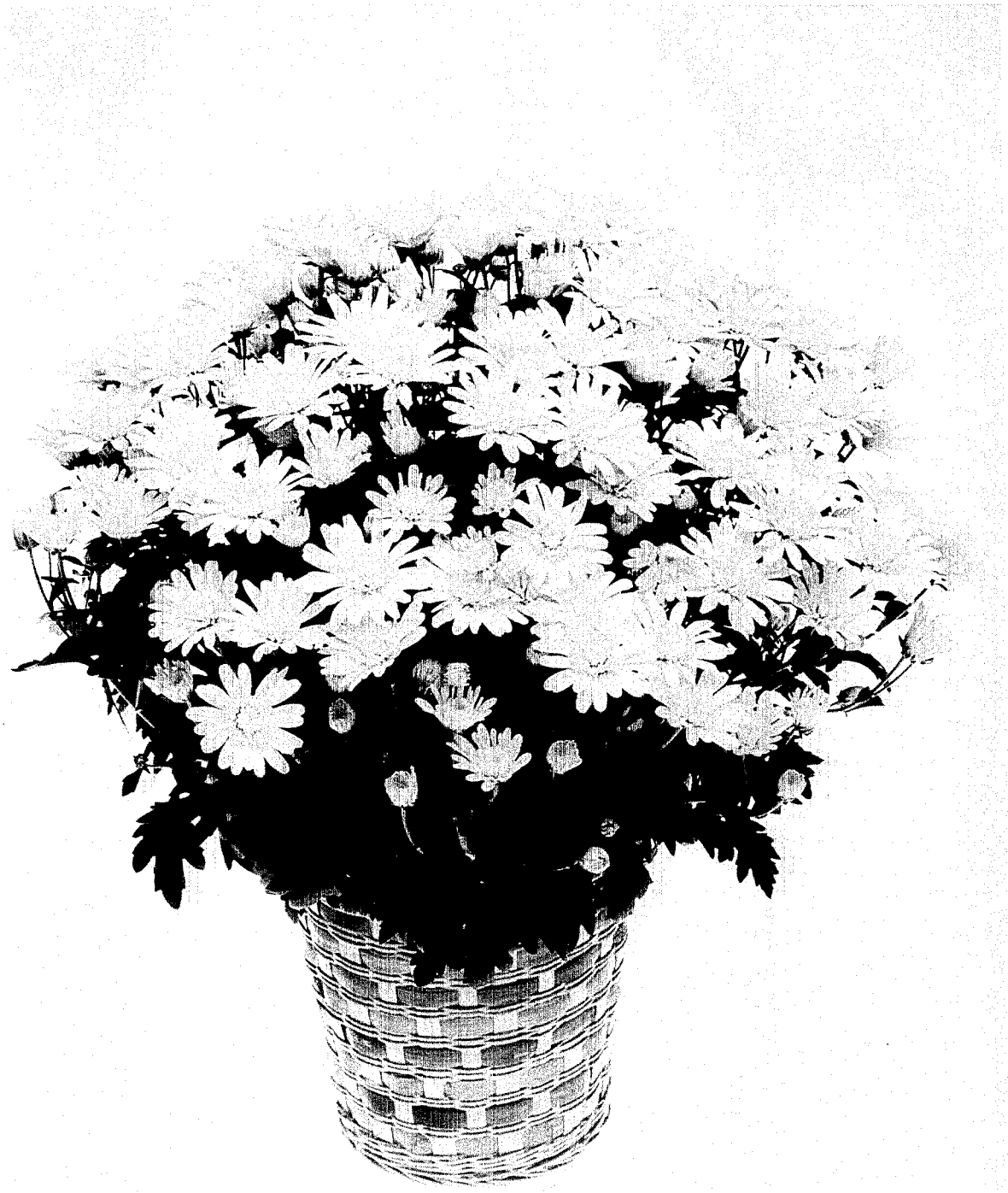

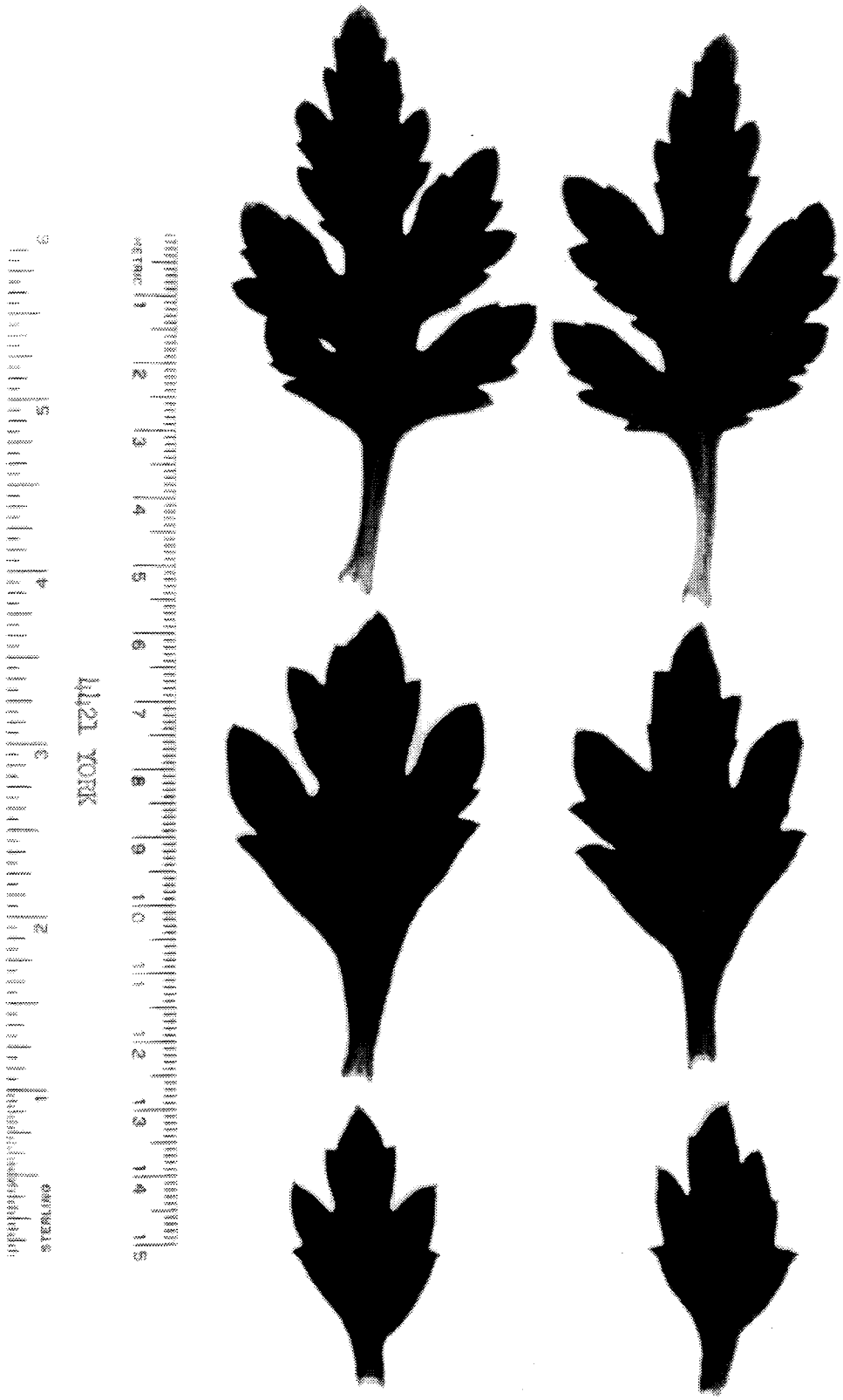
NEW YORK

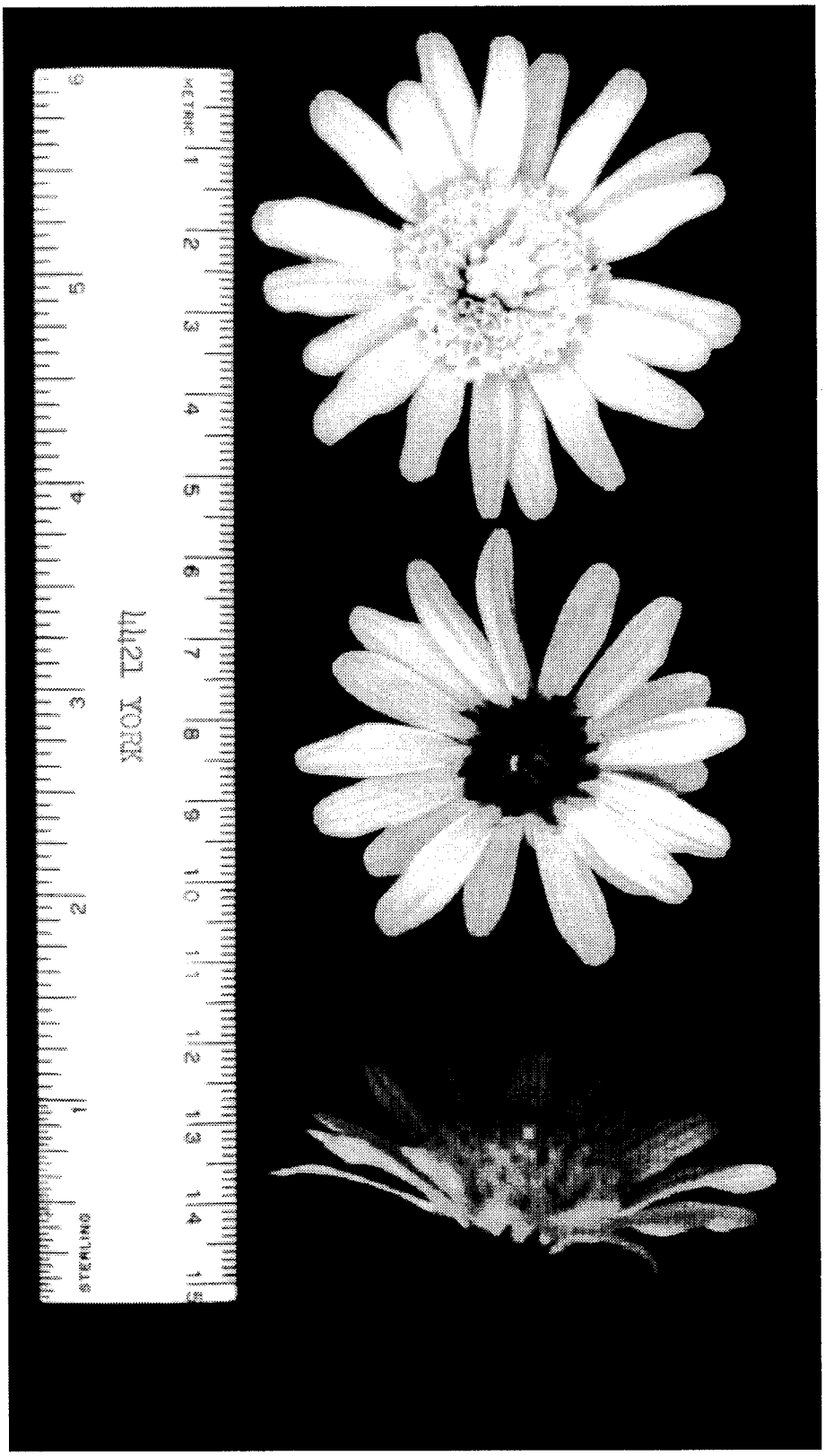
YORK
STERLING